United States Patent [19]

Adrian

[11] Patent Number: 5,019,655

[45] Date of Patent: May 28, 1991

[54] METHOD OF PREPARING 4-DICHLOROPHENYL-1-TETRALONES

[75] Inventor: Guy P. Adrian, Givors, France

[73] Assignee: Delalande S.A., Courbevoie, France

[21] Appl. No.: 363,252

[22] Filed: Jun. 8, 1989

[30] Foreign Application Priority Data

Jun. 8, 1988 [FR] France .................... 88 07641

[51] Int. Cl.$^5$ .................................... C07C 45/45
[52] U.S. Cl. ........................................ 568/322
[58] Field of Search ............................. 568/322

[56] References Cited

U.S. PATENT DOCUMENTS 4,029,731  6/1977  Sarges ........................ 424/316
4,045,488  8/1977  Sarges ........................ 424/330

FOREIGN PATENT DOCUMENTS 0030081  6/1981  European Pat. Off. ......... 424/330

OTHER PUBLICATIONS

Repinskaya et al., J. Org. Chem. U.S.S.R., vol. 18, pp. 754–760, (1984).
Koptyug et al., Chem. Abst., vol. 76, #140, 2865 (1972).

*Primary Examiner*—James H. Reamer
*Attorney, Agent, or Firm*—Foley & Lardner

[57] ABSTRACT

Method of preparing 4-disubstituted phenyl-1-tetralones of formula

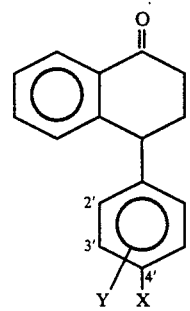

in which X represents halogen, $C_1$–$C_4$ alkyl or $C_1$–$C_4$ alkoxy and Y, situated in position 2' or 3', represents halogen or $C_1$–$C_4$ alkyl, this method being characterized in that it comprises the reaction, in the presence of an acid agent, of α-naphthol of formula (II) with a phenyl compound of formula (III):

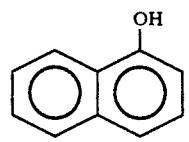

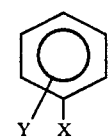

where X represents halogen, $C_1$–$C_4$ alkyl or $C_1$–$C_4$ alkoxy, and Y is situated in the ortho or meta position with respect to X and represents halogen or $C_1$–$C_4$ alkyl.

12 Claims, No Drawings

METHOD OF PREPARING 4-DICHLOROPHENYL-1-TETRALONES

BACKGROUND OF THE INVENTION

The present invention relates to a method of preparing 4-disubstituted phenyl-1-tetralones, also called 4-disubstituted phenyl-3,4-dihydro-1-(2H) naphthalenones and more precisely 4-disubstituted phenyl-1-tetralones of formula

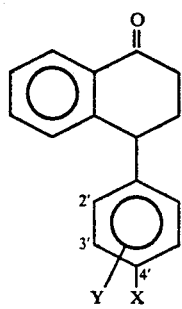

in which
X represents a halogen atom, a $C_1$-$C_4$ alkyl group or a $C_1$-$C_4$ alkoxy group and
Y is situated in position 2' or 3' and represents a halogen atom or a $C_1$-$C_4$ alkyl group.

These tetralones are known for being particularly useful as synthesis intermediates for preparing different serotonine pre-synaptic inhibitor compounds with anti-depressive property, described more particularly in the U.S. Pat. Nos. 4,029,731 and 4,045,488 and the European patent No. 0 030 081.

Up to the present time, the tetralones of formula (I) have been prepared using a method comprising five steps described in Organic Reaction, vol VI, pages 1 to 73 and in the above mentioned European patent. This known method comprises (a) the reaction of benzoyl chloride with an aromatic hydrocarbon in the presence of aluminium chloride, which leads to benzophenones, (b) condensation of the latter, under the conditions of Stobbe's reaction in the presence of a strong base such as potassium tertiobutoxide, with diethyl succinate, (c) decarboxylation of the compounds obtained, using an aqueous hydrobromic acid solution, which leads to 4,4-diaryl butenoic acids, (d) hydrogenation of the latter on palladium charcoal in 4,4-diaryl butanoic acids, and (e) cyclization of the latter in 4-aryl tetralones, either directly by means of hydrofluoric acid or polyphosphoric acid, or, after transformation into acid chlorides using thionyl chloride, by the action of aluminium chloride under the conditions of Friedel-Crafts reaction.

This known method has different drawbacks. In fact, it is extremely long since it comprises five steps which each require a relatively long reaction time. Moreover, it uses expensive reagents such as potassium tertiobutoxide and palladium charcoal, or aggressive agents and so dangerous to use such as hydrobromic acid, hydrofluoric acid and thionyl chloride. Furthermore, because of the large number of steps required, the overall tetralone yield is very low since, in the best of cases, it does not exceed 40% with respect to the benzoyl chloride.

All these drawbacks undeniably form major obstacles to the industrial use of the method in question.

SUMMARY OF THE INVENTION

The aim of the present invention is consequently to overcome these drawbacks and, for this, it provides a method of preparing tetralones corresponding to the above defined formula (I), which method is characterized in that it comprises the reaction, in the presence of an acid agent, of α-naphthol of formula:

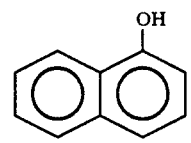

with a phenyl compound of formula:

in which:
X represents a halogen atom, a $C_1$-$C_4$ alkyl group or a $C_1$-$C_4$ alkoxy group, and
Y is situated in the ortho or meta position with respect to X and represents a halogen atom or a $C_1$-$C_4$ alkyl group.

DETAILED DESCRIPTION OF PREFERRED EMBODIMENTS

As may be seen, the method of the invention is of a particularly simple conception since it only comprises a single step which is easy, rapid and inexpensive to put into practice and does not require any special precaution since it does not make use of dangerous reagents. In addition, it makes it possible to obtain the desired tetralones with extremely high yields reaching 80% with respect to the α-naphtol; this method forms then a method of choice for the industrial preparation of such tetralones.

It should be noted that in the foregoing and in what follows, the expression "halogen atom" comprises the fluorine, chlorine, bromine and iodine atoms; the expression "$C_1$-$C_4$ alkyl" comprises the linear or branched, hydrocarbon groups comprising 1 to 4 carbon atoms, namely the methyl, ethyl, n-propyl, iso-propyl, n-butyl, iso-butyl, sec-butyl and tert-butyl groups; and the expression "$C_1$-$C_4$ alkoxy" corresponds to the formula "O—$C_1$-$C_4$ alkyl".

The acid agent used in the method of the invention is advantageously formed by a Lewis acid, particularly an aluminium tri-halide and in particular the Lewis acid is chosen from aluminium chloride, aluminium bromide and mixtures thereof.

Furthermore, it is preferable for the compound of formula (III) to be used in excess with respect to the compound of formula (II), the best yields being obtained when the compound of formula (III) is used at the ratio of 2 to 10, and in particular 2 to 5, molar equivalents with respect to the compound of formula (II).

As for the acid agent, it is generally used at the ratio of 1.5 to 3 molar equivalents with respect to the compound of formula (II), a particularly preferred embodiment consisting in using, as acid agent, about 2 moles of aluminium chloride per mole of the compound of formula (II).

The reaction of the compound of formula (II) with the compound of formula (III) is preferably carried with heating, for example between 40° and 100° C. and particularly between 50° and 70° C.

The phenyl compound of formula (III), used in excess, may play the role of solvent and the reaction may then for example be carried out indifferently by introduction of the acid agent into an α-naphthol (II) suspension in the phenyl compound (III) or by the addition of α-naphthol in a suitably agitated suspension of the acid agent in the phenyl compound (III). However, nothing prevents the reaction from being carried out in an organic solvent which will be preferably chosen from the polyhalogenated aliphatic hydrocarbons and mixtures thereof, this solvent being for example formed by 1,2-dichloro ethane.

The reaction is generally completed after 1 to 3 hours. This time is however variable depending on the reaction temperature and on the amount of acid agent and compound (III) used with respect to compound (II).

In accordance with the present invention, the reaction product of the compound of formula (II) with the compound of formula (III) is then subjected to hydrolysis, by water or water acidified for example by means of hydrochloric acid, particularly at a temperature less than 40° C.

The desired tetralones may be isolated and purified using conventional techniques well known to a man skilled in the art and particularly by distillation elimination of the excess phenyl compound (III), the latter being advantageously recycled, followed by isolation of the tetralone, either by distillation or by crystallization in an appropriate solvent.

In the method of the invention, the compound of formula (III) may in particular be chosen from those for which the pair (X,Y) takes the value (Cl, 2-Cl) or (Cl, 3-Cl), the compounds of formula (I) obtained by using these particular compounds of formula (III), making possible the preparation of final particularly interesting compounds having anti-depressive property.

The invention is illustrated hereafter by a number of examples.

EXAMPLE 1

Preparation of 4-(3′,4′-dichlorophenyl)-3,4-dihydro-1-(2H)-naphthalenone

In a 1 liter reactor, equipped with a rotary anchor agitation device, are placed 144.2 g (1 mole) of α-naphthol and 500 ml of orthodichlorobenzene. In 20 minutes and by portions, 280 g (2.1 moles) of anhydrous aluminium chloride are added. The temperature rises from 20° to 50° C. and the thick yellow suspension is progressively dissolved to give a green solution.

The reaction medium is heated for 3 hours at 65° C., then it is poured on 1500 ml of water. The lower organic phase is separated by decantation and the aqueous phase re-extracted with 300 ml of orthodichlorobenzene.

The organic phase is concentrated in a vacuum at a temperature between 60° and 80° C. under a pressure of 2 to 5 torrs and the orthodichlorobenzene thus recovered, namely 650 ml, may be recycled. The concentrate (about 300 g) is taken up with 400 ml of methyl ethyl ketone and 2 g of discoloring charcoal at 60° C., then filtered and diluted with 250 ml of methanol. The solution is cooled for 4 hours at 0° C. The light beige solid formed is separated by filtration and dried, which gives 177.8 g of the expected compound.

Yield 61% with respect to the starting α-naphthol.
Melting point: 104°–105° C.
CGL purity: 98–99%

A CGL purity greater than 99.5% may be obtained by recrystallization in a mixture of 2 parts of methyl ethyl ketone and 2.5 parts of methanol.

EXAMPLE 2

Preparation of 4-(3′,4′-dichlorophenyl)-3,4-dihydro-1-(2H)-naphthalenone

In a suspension of 280 g (2.1 moles) of anhydrous aluminium chloride in 500 ml of orthodichlorobenzene, 144.2 g (1 mole) of α-naphthol are introduced in 20 minutes. The medium is heated for 3 hours at 65° C., then hydrolysed at a temperature less than 40° C. with 1 liter of water.

700 ml of di-isopropylic ether is added, the mixture is decanted and the upper organic phase is separated which is maintained for 4 hours between −5° and −10° C.

The precipitate formed is separated and dried to obtain 148 g of the expected compound.
Yield: 50.9% with respect to the α-naphthol
Melting point: 105° C.
CGL purity: 99%

EXAMPLE 3

Preparation of 4-(3′,4′-dichlorophenyl)-3,4-dihydro-1-(2H)-naphthalenone

In a solution of 100 g (0.374 mole) of anhydrous aluminium bromide in 130 ml of orthodichlorobenzene, 28 g (0.194 mole) of α-naphthol are added. The green solution obtained is heated for 1 hour at 65° C. then hydrolysed with 400 ml of water at 40° C. After decantation, the organic phase is separated which is concentrated under a vacuum. After crystallization of the residue in 140 ml of methanol at 0° C. for 2 hours, 45 g of the expected compound are obtained after filtration and drying.

Yield: 79.6% with respect to the α-naphthol
Melting point 104° C.
CGL purity: 98.5%

EXAMPLE 4

Preparation of 4-(2′,4′-dichlorophenyl)-3,4-dihydro-1-(2H)-naphthalenone

In a suspension of 60 g (0.45 mole) of aluminium chloride in 100 ml of metadichlorobenzene, 28.8 g (0.2 mole) of α-naphthol are introduced in 10 minutes: the temperature rises from 20° to 45° C. The medium is heated for 1 hour 30 mins at 65° C. then hydrolysed with 400 ml of water. After decantation, the organic phase is separated and concentrated in a vacuum from 2 to 5 torrs at 80° C. The residue is dissolved in 100 ml of isopropanol and the resultant solution cooled at 0° C. for 2 hours. The light beige solid formed is separated by filtration and dried to obtain 41.5 g of the expected compound.

Yield: 71% with respect to the α-naphthol

Melting point: 123°-124° C.
CGL purity: 99%
NMR spectrum (CDCl$_3$), δ (ppm): 2,20-2,80 (m, 4H); 4,80 (t, 1H); 6,80-8,10 (m, 7H)

What is claimed is:

1. A method of preparing 4-dichlorophenyl-1-tetralones having the formula (I)

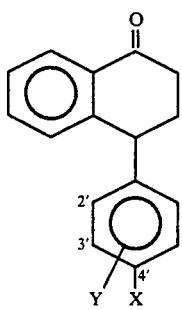

wherein:
—X and Y each represent a chlorine atom, and Y is situated in position 2' or 3',
said method comprising the step of reacting α-naphthol with ortho-dichlorobenzene or meta-dichlorobenzene, in the presence of an acid agent.

2. The method according to claim 1, which further comprises the step of hydrolyzing the product obtained by reacting α-naphthol with ortho-dichlorobenzene or meta-dichlorobenzene.

3. The method according to claim 2, wherein said hydrolysis is an acid hydrolysis.

4. The method according to claim 1, wherein said acid agent is a Lewis acid.

5. The method according to claim 4, wherein said Lewis acid is an aluminum tri-halide.

6. The method according to claim 4, wherein said Lewis acid is aluminum chloride, aluminum bromide or a mixture thereof.

7. The method according to claim 1, wherein said ortho-dichlorobenzene or meta-dichlorobenzene is used in excess with respect to said α-naphthol.

8. The method according to claim 7, wherein said ortho-dichlorobenzene or meta-dichlorobenzene is used in a ratio of 2 to 5 molar equivalents with respect to said α-naphthol.

9. The method according to claim 1, wherein said acid agent is used in a ratio of 1.5 to 3 molar equivalents with respect to said α-naphthol.

10. The method according to claim 9, wherein said acid agent is aluminum chloride used in a ratio of 2.1 moles per mole of said α-naphthol.

11. The method according to claim 1, wherein said reaction of α-naphthol with ortho-dichlorobenzene or meta-dichlorobenzene is carried out at a temperature of between 50° and 70° C.

12. The method according to claim 1, wherein said reaction of α-naphthol with ortho-dichlorobenzene or meta-dichlorobenzene is effected in an organic solvent which is a polyhalogenated aliphatic hydrocarbon or a mixture of polyhalogenated aliphatic hydrocarbons.

* * * * *